US00PP35811P2

(12) United States Plant Patent
Kordes

(10) Patent No.: US PP35,811 P2
(45) Date of Patent: May 21, 2024

(54) MINIATURE ROSE PLANT NAMED 'KORPOT121'

(50) Latin Name: *Rosa hybrida*
Varietal Denomination: KORpot121

(71) Applicant: W. KORDES' SÖHNE ROSENSCHULEN GMBH & CO KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/385,015

(22) Filed: Oct. 30, 2023

Related U.S. Application Data

(60) Provisional application No. 63/420,731, filed on Oct. 31, 2022.

(51) Int. Cl.
*A01H 5/02* (2018.01)
*A01H 6/74* (2018.01)

(52) U.S. Cl.
USPC ..... Plt./117
CPC ..... *A01H 6/749* (2018.05)

(58) Field of Classification Search
USPC ..... Plt./101, 116, 117
See application file for complete search history.

(56) References Cited

U.S. PATENT DOCUMENTS

PP28,499 P3 10/2017 Kordes
PP30,787 P3 8/2019 Kordes

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot121', is described. The new variety forms in abundance on a substantially continuous basis attractive, white-colored blossoms. The vegetation is vigorous, and the growth habit is compact. Attractive semi-glossy foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORpot121'.

STATEMENT REGARDING PRIOR DISCLOSURES BY THE INVENTOR

The first offer for sale of the new variety was November 2021, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2017 at Offenseth-Sparrishoop, Germany by artificial pollination wherein two parents were crossed which previously had been studied in the hope that they would contribute the desired characteristics. The female parent (i.e., the seed parent) of the new variety was the 'RUIpf0499a' (not patented). The male parent (i.e., the pollen parent) of the new variety was the 'KORpot079' variety (U.S. Plant Pat. No. 30,787).

The parentage of the new variety can be summarized as follows:

'RUIpf0499a'×'KORpot079'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrishoop, Germany by a number of routes such as vegetative cuttings. Asexual propagation techniques in Klein Offenseth-Sparrishoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms attractive, white-colored blossoms,
(b) exhibits a compact growth habit, and
(c) forms vigorous vegetation.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'RUIpf0499a' (i.e., the seed parent) displays a smaller flower size compared to the new variety. Additionally, the new variety provides a larger flower size and a higher petal count compared to the 'KORpot079' variety (i.e., the pollen parent). Moreover, the new variety can be readily distinguished from non-parental related similar varieties. For example, 'KORpot068' (U.S. Plant Pat. No. 28,499) displays flowers which are a less pure white and provides a less compact growth habit compared to the new variety.

The new variety has been named the 'KORpot121' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately twelve weeks of age and was grown indoors on its own roots in 10.5 cm containers in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on two-years-old specimens of the new variety, observed during September, while growing in a 3-gallon container on its own roots in a greenhouse in Cochranville, Pennsylvania.

Botanical classification: *Rosa hybrida* cultivar 'KORpot121'.

Commercial classification: Miniature Rose.

Plant:

*Habit*.—Compact.

*Height*.—Approximately 36.0 cm on average from the top of the soil plane in 3-gallon pot.

*Width*.—Approximately 40.0 cm on average.

Branches:

*Stems*.—Color: new wood is commonly Green Group 143A; old wood is commonly Yellow-Green Group 146A. Length: Main stems: approximately 36.0 cm on average. Secondary stems: approximately 15.0 cm on average. Diameter: Main stems: approximately 1.0 cm on average. Secondary stems: approximately 3.0 mm on average. Texture: Glabrous.

*Thorns*.—Young Thorns: Amount: Moderate and small to medium. Color: commonly Yellow-Green Group 145C. Size: Length: approximately 4.0 mm on average. Width: commonly 1.0-2.0 mm at point of attachment. Old Thorns: Amount: Moderate and small to medium. Color: commonly Greyed-Orange Group 165B. Size: Length: approximately 4.0 mm on average. Width: approximately 2.0 mm at point of attachment.

Foliage:

*Color* (*young foliage*).—Upper Surface: commonly Green Group 137C with indistinguishable venation. Under Surface: commonly a blend of Yellow-Green Group N148A and Greyed-Orange Group 176C with venation of Yellow-Green Group 146C.

*Color* (*old foliage*).—Upper Surface: commonly Green Group 139B with indistinguishable venation. Under Surface: commonly Green Group 138B with venation of Green Group 139C.

*Leaf margin*.—Serrate.

*Leaflets*.—Number: 3, 5, and 7. Shape: Ovate. Apex: Acute. Base: Rounded. Arrangement: Odd-pinnate. Texture: Upper Surface: Smooth. Under Surface: Smooth. Venation pattern: Reticulate. Glossiness of upper side of leaf: Semi-glossy. Size: Terminal Leaflet Length: approximately 3.0 cm on average. Width: approximately 2.0 cm on average. Lower Leaflets Length: approximately 2.5 cm on average. Width: approximately 1.5 cm on average. 5-Leaflet leaf Length: approximately 7.0 cm on average. Width: approximately 5.0 cm on average. Undulation of leaf margin: Moderate.

*Petiole*.—Length: approximately 2.0 cm on average. Diameter: approximately 2.0 mm on average. Texture: Upper surface: Smooth. Under surface: Mostly smooth with sparse prickles. Color: Upper surface: commonly Green Group 143A. Under surface: commonly Green Group 143B.

*Rachis*.—Length: approximately 3.5 cm on average. Diameter: approximately 1.0 mm on average. Color: Upper surface: commonly Green Group 143A. Under surface: commonly Green Group 143B.

*Stipules*.—Length: approximately 7.0 mm on average. Width: approximately 2.0 mm on average. Margin: Entire to erose. Color: Upper surface: commonly Green Group 143A. Under surface: commonly Green Group 143B.

Inflorescence:

*Number of flowers*.—About 20 blooms on average on a plant at once.

*Number of blossoms per stem*.—Typically, 1 to 3 blooms per stem on average.

*Peduncle*.—Color: commonly Green Group 143A. Diameter: approximately 2.0 mm on average. Length: approximately 3.5 cm on average. Surface Texture: Glabrous. Strength: Strong.

*Sepals*.—Number: 5. Upper surface color and texture: Covered in short pubescence, commonly Green Group 143B. Under surface color and texture: Puberulent, commonly Green Group 143C. Size: Length: approximately 1.5 cm on average. Width: approximately 1.0 cm on average. Margin: Entire with occasional extensions on two or three sepals measuring approximately 7.0 mm in length and approximately 2.0 mm in width. Shape: Lanceolate. Apex: Acute to Aristate. Base: Truncate or flat as it joins the receptacle.

*Buds*.—Shape: Globular. Size: Length: approximately 2.0 cm on average. Width: approximately 2.0 cm on average. Color (when opening): commonly White Group 155A.

*Flower*.—Form: Double, cuplike. Duration: approximately 5.0 cm on average. Height: approximately 2.0 cm on average. Profile: Flat. Duration: On the plant approximately 22 days. Fragrance: Very light sweet Fragrance.

*Petal*.—Color when first and fully open: Upper Surface: commonly White Group NN155A with basal spot of White Group 155B. Under Surface: commonly White Group NN155A with basal spot of White Group 155B. Color when fading: Upper and Under Surface: commonly White Group NN155B. Petal Texture of upper and lower surfaces: Glabrous. Petal Margin Undulation: Moderate. Petals reflex one by one: Yes. Petal number: 92 on average. Petal drop: Average for the type. Length: Inner Petals: approximately 1.0 cm on average. Outer Petals: approximately 2.5 cm on average. Width: Inner Petals: approximately 8.0 mm on average. Outer Petals: approximately 2.0 cm on average. Overall Shape: Broadly obovate. Margin: Entire. Apex Shape: Rounded to cuspidate. Base Shape: Rounded to cuneate.

*Petaloids*.—Number: On average, 5 per flower. Color: Upper and under surfaces: commonly White Group NN155B with basal spot of Yellow Group 4D. Length: Approximately 5.0 mm on average. Width: Approximately 3.0 mm on average. Texture: Smooth. Margins: Variable, entire to erose. Shape: Rounded and mostly curving inward. Apex: Round. Base: Cuneate.

*Stamen*.—Number: Approximately 80. Anthers — Number: Approximately 80. Color: commonly Greyed-Yellow Group 162A. Shape: Oval. Length: Approximately 1.5 mm on average. Filaments — Length: Approximately 1.5 mm on average. Color: commonly Green-Yellow Group 1B.

*Pistils*.—Arrangement: Separate and free. Number: Approximately 96. Style: Color: commonly Green-Yellow Group 1B at the base, transitioning to White Group NN155B at the apex. Length: Approximately 5.0 mm on average. Stigma: Color: commonly Green-Yellow Group 1B. Diameter: Less than 1.0 mm. Shape: Fan Shaped.

*Receptacle*.—Diameter: approximately 6.0 mm on average. Depth: approximately 4.0 mm on average. Shape: Urn shaped. Color: commonly Green Group 143B. Surface Texture: Smooth.

*Pollen*.—None observed.

*Hips/seed formation*.—None observed.

Development:

*Vegetation*.—Dark Green, vigorous, and strong.

*Blossoming*.—Abundant and continuous. Blooms may continue year-round if grown inside a warm greenhouse.

*Hardiness*.—Unknown.

*Resistance to diseases*.—Good resistance to Powdery Mildew (*Sphaerotheca pannosa*) disease under normal greenhouse growing conditions in Cochranville, Pennsylvania.

The new 'KORpot121' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot121' characterized by the following combination of characteristics:

(a) forms attractive, white-colored blossoms, (b) exhibits a compact growth habit, and (c) forms vigorous vegetation;

substantially as herein shown and described.

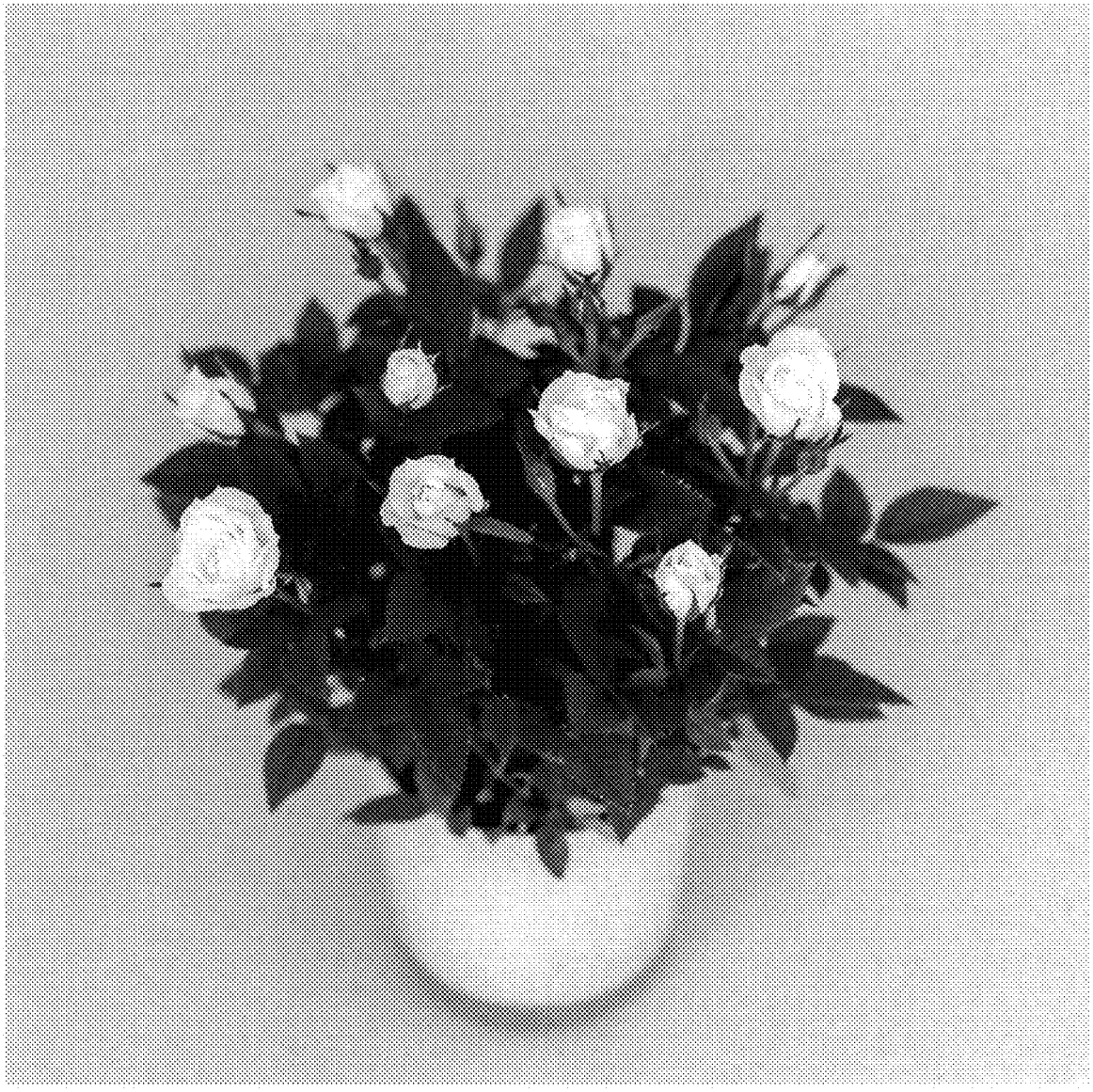

* * * * *